United States Patent [19]

D'Haese et al.

[11] Patent Number: 5,270,111
[45] Date of Patent: Dec. 14, 1993

[54] WATER-DISPERSIBLE PRESSURE SENSITIVE ADHESIVE TAPE

[75] Inventors: Francois C. D'Haese, Lede, Belgium; Katharina J. Bischof, Dusseldorf; Peter Brink, Wuppertal, both of Fed. Rep. of Germany; Yvan A. Bogaert, Gent, Belgium

[73] Assignee: Minnesota Mining and Manufacturing Company, St. Paul, Minn.

[21] Appl. No.: 966,905

[22] Filed: Oct. 27, 1992

Related U.S. Application Data

[63] Continuation of Ser. No. 874,725, Apr. 27, 1992, abandoned, which is a continuation of Ser. No. 580,116, Sep. 10, 1990, Pat. No. 5,125,995.

[51] Int. Cl.$^5$ .......................... C09J 7/04; C09J 11/06; C09J 123/06; A61L 15/24
[52] U.S. Cl. .................................... 428/356; 523/111; 604/387; 604/389
[58] Field of Search ...................... 428/356; 523/111; 604/387, 389

[56] References Cited

U.S. PATENT DOCUMENTS

| | | |
|---|---|---|
| 2,838,421 | 6/1958 | Sohl . |
| 3,096,202 | 7/1963 | de Groot von Arx . |
| 3,152,940 | 10/1964 | Abel et al. ............... 156/157 |
| 3,321,451 | 5/1967 | Gander . |
| 3,441,430 | 4/1969 | Peterson . |
| 3,763,117 | 10/1973 | McKenna, Jr. et al. . |
| 3,790,533 | 2/1974 | Samour . |
| 3,865,770 | 2/1975 | Blake . |
| 3,890,292 | 6/1975 | Bohme et al. . |
| 3,983,297 | 9/1976 | Ono et al. ................ 428/355 |
| 4,033,918 | 7/1977 | Hauber et al. . |
| 4,341,680 | 7/1982 | Hauber et al. ............ 525/329 |
| 4,352,359 | 10/1982 | Larimore et al. ........ 128/640 |
| 4,379,881 | 4/1983 | Peck ........................ 524/315 |
| 4,388,432 | 6/1983 | Eskay ...................... 524/388 |
| 4,413,080 | 11/1983 | Blake ....................... 524/187 |
| 4,413,082 | 11/1983 | Gleichenhagen et al. 524/243 |
| 4,442,258 | 4/1984 | Sunakawa et al. ...... 524/767 |
| 4,539,996 | 9/1985 | Engel ....................... 128/640 |
| 4,569,960 | 2/1986 | Blake ....................... 524/145 |
| 4,728,568 | 3/1988 | Sasada et al. ............ 428/349 |
| 5,125,995 | 6/1992 | D'Haese et al. ......... 156/155 |

FOREIGN PATENT DOCUMENTS

| | | |
|---|---|---|
| 0147067 | 11/1984 | European Pat. Off. . |
| 0172724 | 8/1985 | European Pat. Off. . |
| 0297451 | 6/1988 | European Pat. Off. . |
| 0352442 | 6/1989 | European Pat. Off. . |
| 0379932 | 1/1990 | European Pat. Off. . |
| 2142770 | 8/1971 | Fed. Rep. of Germany . |

OTHER PUBLICATIONS

United States Patent Application Ser. No. 07/878,289 (Reissue).

*Primary Examiner*—James C. Cannon
*Attorney, Agent, or Firm*—Gary L. Griswold; Walter N. Kirn; John H. Hornickel

[57] ABSTRACT

A method of using a pressure sensitive adhesive to form a moisture resistant, water-dispersible tape is provided. The adhesive and tape are resistant to autoclavation conditions and/or moisture and body fluids during usage, and are water-dispersible when immersed in aqueous solutions. The tape may be used with cloth body coverings, such as garments such as hospital gowns, drapes, dressings, diapers and other body coverings which require cloth to cloth or cloth to skin adhesion in the presence of moisture and bodily fluids yet be dispersible from such body coverings during laundering or other aqueous alkali immersion.

7 Claims, No Drawings

WATER-DISPERSIBLE PRESSURE SENSITIVE ADHESIVE TAPE

This is a continuation of application Ser. No. 07/874,725, filed Apr. 27, 1992, now abandoned, which is a continuation of application Ser. No. 07/580,116, filed Sep. 10, 1990, now U.S. Pat. No. 5,125,995.

FIELD OF THE INVENTION

This invention relates to water-dispersible pressure sensitive adhesives and the use of such pressure sensitive adhesives on tape to adhere to cloth used as mammalian body coverings.

BACKGROUND OF THE INVENTION

Cloth has been fashioned into a variety of garments (e.g., clothes and gowns used in hospitals), medical drapes and dressings, diapers, and other useful mammalian body coverings. Cloth is defined in its broadest sense to be fabric or material formed by weaving, knitting, knotting, pressing, bonding, crocheting, interlocking, interlacing, melt-blowing, or felting of natural or synthetic yarns, filaments, or fibers. Nonlimiting examples of cloth include woven, knitted or non-woven fabrics and webs, used as body coverings.

The traditional methods of fastening one portion of the cloth to another portion of the cloth have included strings, buttons, zippers, pins, snap fasteners, and hook and loop fasteners. Such fastening means conventionally used may be bulky, unwieldy, or incompatible with the necessity of adhering cloth to the skin of individuals wearing the body covering or to other portions of the cloth for easy and rapid securement. For example, in surgical arenas, one or more cloth drapes may be employed to cover portion(s) of a patient undergoing surgery. Some drapes must be adhered to a patient's skin. other drapes are often fastened to the drapes adhered to the skin. Conventional forms of mechanical fastening are inappropriate or inconvenient.

Pressure sensitive adhesive tapes have been used with garments, drapes and dressings, and diapers which are meant to be disposed after a single use as solid waste. Examples of pressure sensitive adhesive tapes which have been employed for such disposable items include water insoluble styrene-isoprene-styrene block copolymers with tackifying resins, vinyl ethers, and high molecular weight acrylate copolymers having minimal amounts of plasticizing monomer therein.

Cloth for body coverings may be disposed or retained after use. If retained, soiled cloth must be cleaned after use, usually by laundering in soapy water, an aqueous alkali solution. For medical and surgical use, the cloth must also be sterilized by autoclavation after laundering and before use. The expense of some cloth such as linen demands that the fastening means also be reusable or replaceable at a reasonable cost.

Various mechanical fastening means subjected to repeated sterilizations in an autoclave may not survive repeated cleanings. The mechanical fastening means may be too expensive to be replaced for each repeated use of the cloth. Pressure sensitive adhesive tapes presently useful for disposable garments, drapes, dressings and diapers are not formulated to endure repeated use under such sterilizing and cleaning conditions. And such pressure sensitive adhesive tapes do not disperse during cleaning.

Water-dispersible pressure sensitive adhesives have been made for paper making and printing operations which require splicing of the end of one roll of paper to the beginning of another roll.

Examples of such water-dispersible pressure sensitive adhesives include U.S. Pat. Nos. 3,865,770; 4,413,080; and 4,569,960 (Blake), U.S. Pat. No. 3,441,430 (Peterson), and U.S. Pat. No. 2,838,421 (Sohl). Blake discloses water-dispersible pressure sensitive adhesives for splicing carbonless paper which comprise a blend of acrylate:acrylic acid copolymers and systems which include tackifiers, plasticizers, and neutralizers. Peterson discloses aggressively water soluble tacky adhesives composed of a copolymer of a mono-carboxylic acid and an alkoxy-alkyl ester, a plasticizer having at least one ether linkage, a cross linker, and up to two parts of a copolymer of the hydroxide of a monovalent cation. The hydroxide is used to neutralize sulfuric acid generated during the decomposition of a potassium persulfate catalyst used for copolymerization. Sohl discloses a mixture of water-soluble polyvinyl carboxylic acid and a compatible hydroxy-polyalkylene permanent elasticizer which retains adequate tackiness and internal, cohesive strength even when exposed for a week or more at humidities in the range from 0 to 90% relative humidity.

Two other water soluble pressure sensitive adhesive compositions are disclosed in U.S. Pat. No. 4,413,082 (Gleichenhagen et al.) and U.S. Pat. No. 4,341,680 (Hauber et al.). Gleichenhagen et al. discloses a composition comprising a copolymer of acrylic acid butyl ester and vinyl carboxylic acid, and a plasticizer. The copolymer, which contains free carboxyl groups is neutralized almost completely by the addition of potassium hydroxide, preferably in excess. Gleichenhagen et al. discloses the neutralization with potassium hydroxide normally brings about an excellent solubility of the pressure sensitive adhesive composition in water, even at widely varying pH values, but also exerts a strongly positive influence on the adhesive properties (especially tack and cohesion) which can be further enhanced by over-neutralization (use of an excess of KOH). Hauber et al. discloses a mixture of a copolymer of a monomeric ethyl acrylate and a monomeric $\alpha$, $\beta$ unsaturated aliphatic monocarboxylic acid and a tertiary, ethoxylated n-alkyl alkane diamine, where from 50% to 90% of the acid groups of the monocarboxylic acid are neutralized.

Another water soluble pressure sensitive pressure adhesive composition for papermaking tapes is disclosed in European Patent Publication 0 352 442 (Zbigniew Czech). The composition is a water-soluble contact adhesive based on a polyvinyl carbonic acid with at least one softener containing a hydroxyl group with a molecular weight below 1000 and curing agents used to process paper.

Another water-soluble pressure sensitive adhesive composition for photographic papermaking repulpable tapes is disclosed in U.S. Pat. No. 3,152,940 (Abel et al.) The preferred composition is an alkali-soluble copolymer of acrylic acid ester and acrylic acid and a water-soluble wax of hydroxy polyalkylene material which remains cohesive and tacky when exposed either to dry or humid atmospheric conditions.

Another repulpable acrylic acid based pressure sensitive adhesive is disclosed in U.S. Pat. No. 4,388,432 (Eskay). The composition for making water-dispersible tapes for papermaking is a copolymer of an acrylic acid compound, which is a homopolymer of acrylic acid or a copolymer of acrylic acid and esters of acrylic acid or methacrylic acid, a polyhydric alcohol plasticizer-tackifier, and a minor amount of monobasic caustic. Amounts of the base higher than 2.5 pecent cause the adhesive to become elastic in nature rather than tacky.

Another water-soluble pressure sensitive adhesive for papermaking tapes is disclosed in U.S. Pat. No. 3,096,202 (degroot von Arx). Polyvinylpyrrolidone, a polyfunctional monomeric cross-linking agent, a compatible plasticizer, and an activator catalyst to induce vinyl-type polymerization are combined to produce a water-soluble, normally tacky pressure sensitive adhesive retaining its adhesiveness after subjection to elevated temperatures.

European Patent Publication 0 297 451 (Knutson et al.) discloses a hot melt adhesive activated by moisture which is water soluble and alkali dispersible to be recycled with paper products. The hot melt adhesive comprises an N-acyl-polyalkyleneimine and an acid functional compound.

Another water soluble adhesive useful with paper products such as decals, labels, and bumper stickers is disclosed in U.S. Pat. No. 3,763,117 (McKenna et al.). The composition which has aggressive tack and aqueous alkali removability comprises a hydroxy bearing monomer, a softening acrylate or methacrylate comonomer, and optionally, a hardening comonomer of either vinyl esters of alkanoic acids, ethyl or methyl acrylates, ethyl or methyl diesters of maleic or fumaric acids, acrylonitrile, methacrylonitrile, styrene, or vinyl chloride.

A transfer or splicing tape is disclosed in U.S. Pat. No. 3,890,292 (Bohme et al.). The tape is formed with a water dispersible adhesive composition of ionomeric copolymers of hydrophilic and hydrophobic monomers. The ionic monomer comprises a water soluble alkali metal salt of an $\alpha, \beta$ unsaturated monocarboxylic acid. The water soluble nonionic monomers are polyalkylene oxide condensation products. The composition maintains excellent tack characteristics at both high and low humidities and have improved moisture stability properties.

Each of these prior water-dispersible or water-soluble pressure sensitive adhesives has been used in paper making or with paper products not used as mammalian body coverings, although passages in the Blake patents and the Peterson patent also identify use with cloth labels coated with water-dispersible or water-soluble adhesive, respectively, which may be readily washed from garments to which they are affixed.

The sensitivity of mammalian skin to chemicals which contact the skin requires specific compositions to minimize allergic or toxic reaction between the adhesive components and the sensitive skin of the individual. Commercially available tackifiers useful for industrial operations such as papermaking can generate allergic or toxic reactions when compositions comprising such industrially acceptable tackifiers are placed in contact with mammalian skin.

Prior use of disposable mammalian body coverings, e.g., garments, drapes and dressings, and diapers hat been found to increase environmental concerns and solid waste disposal issues. Reusable cloth body coverings, e.g., garments such as hospital gowns, drapes and dressings, and diapers have economic and environmental advantages. But the use of cloth items must be tempered by the ability to find a suitable fastening system.

SUMMARY OF THE INVENTION

None of the water-dispersible or water-soluble pressure sensitive adhesives previously disclosed has been contemplated for use as moisture resistant tapes for cloth body coverings. As used herein, "cloth body coverings" means body coverings made of at least some portion of cloth and designed for use with mammals. Preferably, but not necessarily, the cloth body covering is reusable.

The present invention uses water-dispersible pressure sensitive adhesives to form tapes which retain pressure sensitive adhesive properties after or during exposure to moisture and body fluids likely to be encountered on or near mammalian skin. And then such tapes disperse upon immersion in aqueous alkali solutions such as during laundering. Preferably, but not necessarily, the immersion occurs at elevated temperatures and considerable agitation, such as prevalent during a hot water laundry cycle.

The present invention provides a method of using water-dispersible pressure sensitive adhesives to form tapes which are both moisture resistant during use and water-dispersible after use.

The method comprises using a water-dispersible pressure sensitive adhesive tape for a cloth body covering to adhere cloth to cloth or mammalian skin notwithstanding exposure of the adhesive to moisture and body fluids. The method comprises adhering one portion of the pressure sensitive adhesive tape to cloth and another portion of the pressure sensitive adhesive tape to either other cloth or mammalian skin to use the cloth during exposure to moisture and body fluids.

The pressure sensitive adhesive tape comprises a water-dispersible pressure sensitive adhesive coated on at least one surface of a water-dispersible substrate.

The pressure sensitive adhesive is formed from a blend of (a) 100 parts by weight of a copolymer of monomers of (1) about 50–85 weight percent of at least one monomeric acrylic acid ester of nontertiary alkyl alcohol having 2–8 carbon atoms, and (2) about 50–15 weight percent of a vinyl carboxylic acid, (b) about 10 to about 250 parts by weight of a water-dispersible or water-soluble plasticizer, (c) optionally from about 0 to about 100 parts by weight of an acrylate-compatible tackifier not irritating or toxic to mammalian skin; and (d) sufficient alkali metal hydroxide, if any, to neutralize from 0 to no more than 50 percent of acid moieties in the copolymer, to cause the adhesive to retain pressure sensitive adhesive properties during exposure to moisture and body fluids yet be dispersible in aqueous alkali solutions.

The present invention also provides a cloth body covering likely to be exposed to body fluids. The cloth body covering comprises a moisture resistant, water-dispersible pressure sensitive adhesive tape adhered to the cloth body covering. The tape comprises the water-dispersible pressure sensitive adhesive described the paragraph above coated on at least one surface of a water-dispersible substrate.

The water-dispersible pressure sensitive adhesive has a balance of desired properties of initial adhesion, cohesive bonding, static shear adhesion, tack, and moisture resistance. The desired properties are obtained by controlling the neutralization, if any, of the carboxylic acid moiety in the adhesive. The controlled neutralization yields an adhesive having a proper balance of properties to provide the necessary adhesion and bonding and moisture resistance properties for use on cloth body coverings yet to provide the property of water dispersibility when immersed in an aqueous alkali solution, such as during a laundering cycle or other aqueous alkali processing.

The water-dispersible pressure sensitive adhesive when used according to the present invention provides little or no irritation potential or toxicity to mammalian skin which may contact the pressure sensitive adhesive purposefully or inadvertently as the cloth body covering is placed about the mammalian body.

The water-dispersible pressure sensitive adhesive tape is made by coating one or both sides of a water-dispersible substrate, such as a thin tissue paper, with the pressure sensitive adhesive and placing a protective liner over the pressure sensitive adhesive layer(s).

It is a feature of the invention that in use in contact with mammalian skin, the water-dispersible pressure sensitive adhesive minimizes mammalian skin sensitivation and toxicity.

It is another feature of the invention that the the water-dispersible pressure sensitive adhesive disperses when immersed in aqueous alkali solutions in less than about 40-60 minutes, a range of laundering cycle times.

It is an advantage of the invention that tapes made of the water-dispersible pressure sensitive adhesive used according to the present invention exhibit initial adhesion to fluorochemically-treated linen after autoclavation.

It is an another advantage of the invention that the water-dispersible pressure sensitive adhesive resists moisture and body fluids generated during use of the cloth body covering, to avoid loss of adhesion at the time when the cloth body covering is most needed.

It is another advantage of the invention that the water-dispersible pressure sensitive adhesive is dispersible in a soapy solution within 40-60 minutes after immersion leaving little or no residual material on the cloth being laundered or on the filters of the laundering equipment.

It is another advantage of the invention that the water-dispersible pressure sensitive adhesive tape reduces the time for surgical draping and gowning in the surgical arena.

Various embodiments of the invention are described below.

EMBODIMENTS OF THE INVENTION

Water-Dispersible Pressure Sensitive Adhesive Components

Pressure Sensitive Adhesive Copolymer

The copolymer may be comprised of monomers of about 50-85 weight percent of at least one monomeric acrylic acid ester of non-tertiary alkyl alcohol having 2-8 carbon atoms and correspondingly about 50-15 weight percent of a vinyl carboxylic acid. Of the acrylic acid esters of non-tertiary alkyl alcohols, butyl acrylate is preferred. Of the vinyl carboxylic acids, acrylic acid is preferred.

The copolymer desirably may comprise about 60-80 weight percent of butyl acrylate and correspondingly about 40-20 weight percent of acrylic acid. Preferably, the copolymer of butyl acrylate and acrylic acid has weight percent ratio of 75:25.

The copolymer should have a sufficient inherent viscosity to provide appropriate skin adhesion. The copolymer should have an inherent viscosity from about 1 to about 2 dl/g. Skin adhesion increases with decreasing inherent viscosity. However, below about 1.2 dl/g, the inherent viscosity provides a copolymer which is too tacky for skin adhesion. Desirably, the inherent viscosity range for the copolymer is between about 1.2 and 1.4 and preferably between 1.2 and 1.3 dl/g.

Plasticizer

The plasticizer may be at least one water-dispersible or water-soluble plasticizer, or a combination of them. Nonlimiting examples of water-dispersible or water-soluble plasticizers include a free acid or sodium salt of a complex organic phosphate ester or a colophony (rosin) ester having a Tg lower than the Tg of the pressure sensitive adhesive copolymer. Desirably, the plasticizer may be:

poly(oxy-1,2-ethandiyl),alpha-(nonylphenyl)-omega-hydroxy-phosphate, commercially available under the trademark "Gafac PE 510" from Rhone Poulenc, formerly made by GAF Corporation;

poly(oxy-1,2-ethandiyl),alpha-(nonylphenyl)-omega-hydroxy-phosphate sodium, commercially available under the trademark "Gafac LO 529" from Rhone Poulenc;

poly(oxy-1,2-ethandiyl),alpha-dodecyl-omega-hydroxy-phosphate, commercially available under the trademark "Gafac RD 510" from Rhone Poulenc; or a colophony ester having a Tg of about −35° C., commercially available as a tackifier from Bergvik under the brand "Bevelite L62";

or combinations thereof. If the water-dispersible pressure sensitive adhesive is intended for use with cloth body coverings where skin contact is likely, care should be taken to select a plasticizer which is known or identifiable to provide little or no irritation potential or toxicity to mammalian skin. Preferably, the plasticizer is hypoallergenic and non-toxic to mammalian skin.

Tackifier

The tackifier is an optional additive to the pressure sensitive adhesive. If present, the tackifier is a resin such as an aromatic hydrocarbon resin or a colophony (rosin) acid compatible with acrylate copolymers. Tackifier resins for acrylate copolymers are described in Satas, Ed., Handbook of Pressure Sensitive Adhesives, 2nd. Ed., (Van Nostrand, 1989), Chapters 20-22, the disclosure of which is incorporated by reference. If the water-dispersible pressure sensitive adhesive is intended for use with cloth body coverings where skin contact is likely, care should be taken to select a tackifier for acrylate copolymers which is known or identifiable to provide little or no irritation potential or toxicity to mammalian skin. Preferably, the tackifier is hypoallergenic and non-toxic to mammalian skin.

A preferred colophony acid tackifier is commercially available under the trade name "Foral AX" from Hercules Corporation. A preferred partially hydrogenated methylstyrene hydrocarbon tackifier resin is commercially available under the trade name "Piccolastic A25" from Hercules Corporation. of these two specific tackifiers, a colophony acid tackifier ("Foral AX" from Hercules Corporation) is preferred.

Controlling Properties of the Pressure Sensitive Adhesive Through Optional Neutralization Depending on the amounts of the components blended to form the pressure sensitive adhesive, to maintain optimal properties for the pressure sensitive adhesive during and after use, some acid moieties of the copolymer may have to be neutralized with a neutralizing agent. In some circumstances, no neutralization is necessary, especially if the immersion of the pressure sensitive adhesive occurs in a concentrated aqueous alkali solution.

The pressure sensitive adhesive is the blended product of 100 parts by weight of the copolymer, from about 10 to about 250 parts by weight of one or more plasticizers, optionally from 0 to about 100 parts by weight of an acrylate-compatible tackifier, and sufficient molar amounts, if any, of a neutralizing agent in order to control neutralization of the pressure sensitive adhesive to maintain optimal properties of withstanding autoclavation and/or moisture resistance against body fluids but providing water dispersibility.

Desirably, the pressure sensitive adhesive is the blended product of 100 parts by weight of the copolymer, from about 65 to about 145 parts by weight of plasticizer, from about 20 to about 60 parts by weight of an acrylate-compatible tackifier, and sufficient molar amounts of a neutralizing agent, if any, in order to control neutralization of the pressure sensitive adhesive to maintain moisture resistance against body fluids but provide water dispersibility.

Preferably, for each 100 parts by weight of the copolymer, the plasticizer may comprise about 89 parts by weight and the tackifier may comprise about 23 parts by weight.

If used, the neutralizing agent may be one or more alkali metal hydroxides present in an amount sufficient to cause the pressure sensitive adhesive adhesion properties to withstand either autoclavation prior to usage, (typically 6 minutes at 134° C. at 100% humidity at 2 bar pressure,) or moisture and body fluids during usage, or both. But also, the pressure sensitive adhesive must have sufficient dispersibility in an aqueous alkali solution after the cloth has been used.

If used, the neutralizing agent is present in a molar amount to neutralize not more than 50% of the copolymer acid moiety. It is desirable but not required to use the neutralizing agent in molar amounts sufficient to neutralize from about 10% to about 50% of the copolymer acid moiety. While the plasticizer and tackifier may have acid moieties therein, the present invention finds that the base moiety is more apt to neutralize the copolymer acid moiety because the dissociation constant (pKa) of the copolymer acid moiety in the solvent used to prepare the pressure sensitive adhesive is 2.5 times higher than the pKa of the preferred plasticizer and 7 times higher than the pKa of the preferred tackifier.

Preferably, to achieve a balance of the properties of initial adhesion, bonding cohesion, static shear adhesion, tack, and moisture resistance to autoclavation and during use, yet remain water-dispersible during laundering or other aqueous alkali immersion, the amount of neutralizing agent present in the blended reaction product should be sufficient to neutralize from about 12.5% to about 37.5% of the copolymer acid moiety.

The present invention finds that the property of initial adhesion of the pressure sensitive adhesive to cloth decreases as neutralization percentage increases. Bonding cohesion of the pressure sensitive adhesive remains relatively unchanged with increasing neutralization of the copolymer acid moiety. Static shear adhesion of the pressure sensitive adhesive to cloth increases to a peak at about 50% neutralization and then, for neutralizing agents using NaOH, decreases with increasing neutralization above 50%. Most significantly, moisture resistance increases to a peak at about 25% neutralization and then decreases with increasing neutralization above 25%. Thus, to achieve balance of initial adhesion, bonding cohesion, static shear adhesion, and moisture resistance, sufficient neutralizing agent to neutralize about 25% of the copolymer acid moiety is presently preferred.

The choices described above of copolymer, plasticizer, optional tackifier, and optional alkali metal hydroxide and the respective parts by weight of each determine the balance of properties found desirable for the present invention.

Desirably, to provide moisture resistance during use yet provide water-dispersibility upon immersion in aqueous alkali solutions, the water-dispersible pressure sensitive adhesive has an initial adhesion to cloth of equal to or greater than 0.4 Newtons per 2.54 cm, a cohesive bond to cloth of greater than 1 Newton per 2.54 cm, a shear adhesion to cloth greater than about 0.2 hours/200 g, and a moisture resistance of greater than about 30 seconds at 33° C. and exposed to 200 ml of water.

Preferably, to endure the harsh conditions of autoclavation yet be moisture resistant during use and be dispersible upon immersion in aqueous alkali solutions, the water-dispersible pressure sensitive adhesive should have an initial adhesion to cloth of equal to or greater than 0.6 Newtons per 2.54 cm, a cohesive bond to cloth of greater than 1 Newton per 2.54 cm, a shear adhesion to cloth greater than about 0.4 hours/200 g, and a moisture resistance of greater than about 60 seconds at 33° C. and exposed to 200 ml of water.

Preparation of the Water-Dispersible Pressure Sensitive Adhesive

The monomeric acrylic acid ester of non-tertiary alkyl alcohol and the vinyl carboxylic acid are copolymerized with an azobisisobutyronitrile initiator in accordance with the disclosure of U.S. Pat. No. RE24,906 (Ulrich), the disclosure of which is incorporated by reference herein. The pressure sensitive adhesive is prepared by blending into the resulting copolymer, in order, the plasticizer, the tackifier, (if any is to be added), and the neutralizing agent, (if any is to be added). The blended pressure sensitive adhesive comprises solids in an organic solvent in the range from about 20 percent to about 60 percent solids and preferably from about 40 percent to about 50 percent solids. The preferred organic solvent system comprises ethyl acetate and methanol blended in a range from about 60:40 to about 90:10, and preferably 80:20. Alternatively, water is also added to the solvent system to provide a range of ratios of ethyl acetate:methanol:water of from 60:35:5 to 80:15:5.

As will be apparent from the ranges indicated above in the methods of processing to form the pressure sensitive adhesive, substantial variations in composition are possible. For example, the use of higher percentages of short-chain acrylates in a copolymer tends to increase the hardness of the adhesive, decreasing its tackiness. In such event, it is desirable to use a comparatively higher percentage of plasticizer. On the other hand, high percentages of long chain acrylates increase the tackiness of an adhesive and reduce the need for plasticizers. Similarly, the higher the percentage of vinyl carboxylic acid in the copolymer, the lower the degree of neutralization necessary to insure water dispersibility. Well known acrylate monomers such as isooctyl acrylate may increase the tackiness of the ultimate adhesive and improve its adhesion to cloth and skin.

Water-Dispersible Pressure Sensitive Adhesive Tape

The water-dispersible pressure sensitive adhesive may be applied to one or more surfaces of a water-dispersible substrate to form a tape. The tape may be used by applying one or both sides of the tape to cloth for garments such as gowns, drapes and dressings and diapers which require either autoclavation or heating under elevated humidity short of sterilization, or both, prior to usage. The tape dispersibly separates from such cloth upon immersion in aqueous solutions, such as laundering or other aqueous alkali processing, following usage. Depending on whether it is desired to provide a moisture permeable or a moisture occlusive tape, the underlying substrate may be constructed of a film, tissue, or membrane commercially available and known to those skilled in the art to disperse in an aqueous solution. An example of such materials commercially available includes "Crystex" branded eight pound basis weight tissue paper, commercially available from Crystal Tissue Company, of Middletown, Ohio. Commercially available substrates may be coated on one or both sides to provide single bonding surface or double bonding surface of the water-dispersible pressure sensitive adhesive tape to cloth.

Release liners known to those skilled in the art may cover and protect the exposed surfaces of the pressure-sensitive adhesive between manufacturing and use. Commercially available release liners include paper release liners siliconized with a direct coat of polydimethyl siloxane such as "Akrosil" branded liners, commercially available from Akrosil of Menasha, Wis.; "Daubert" branded liners, commercially available from Daubert Coated Products of Westchester, Ill.; and "Stiknot" branded liners, commercially available from H.P. Smith of Bedford Park, Ill.

The presently preferred construction of a tape uses a pressure sensitive adhesive described as preferred above coated on both sides of "Crystex" branded eight pound basis weight water-dispersible paper tissue carrier and further covered by a "Daubert" sixty or eighty pound siliconized paper release liner.

The tapes may be manufactured on tape rolls for continuous feeding or individually-sized tapes for application to specific cloth body coverings, e.g., garments such as hospital gowns, drapes or dressings, or diapers.

Details of the embodiments of the invention continue in the following examples using the following test procedures.

TEST PROCEDURES

Moisture Resistance

General Procedure

A heat sealer and a strip of autoclaved sample tape are used to prepare a polyethylene "bag". The polyethylene "bag" is made by first cutting out two rectangular sheets of polyethylene with a razor blade and laying them on top of one another. The test tape sample is used to adhere the two sheets of superimposed film together along the edge which is the shorter of the two dimensions. The two longer edges of the bag are formed by heat-sealing the two sheets together on the two opposing longer sides. The heat sealer is of the type commonly used to seal food in plastic bags for freezing, e.g., a "Fermant" 800 heat sealer from Josten and Kettenbaum Company of Bergisch Gladbach, West Germany. The heat sealer produces a heat sealed strip which is 4 mm in width on opposing longer sides of the two sheets. After the heat-sealing has been performed, the edges of the bag which are between the heat-seal and the film edges may be trimmed away somewhat if desired.

The top of the bag is left open. A hole is punched through the two sheets of polyethylene near the center of the top open edge. This serves as a means for supporting the water filled-bag during the test. After 200 ml of water warmed to about 33° C. is filled into the bag, the time is measured for the falling of the first drop through the lower edge of the bag, the lower edge of which contains the test tape specimen. The length of time which the adhesive bond can resist the penetration of water in a volume of 200 ml introduced to the formed vessel at a temperature of about 33° C. is a measurement of the adhesive's resistance to water. An average of six measurements is made.

Procedure for incorporating the test sample into the bag construction

1. Two sheets of 50 micron polyethylene film are cut into rectangles (127×228 mm).
2. Tape test specimens (with both liners intact) are wrapped in a nonwoven wrapping material (Product 5514J from Dexter of Windsorlocks, Conn., consisting of 65% cellulose, 10% polyester, and 25% latex fibers). The autoclave used for all testing procedures was Model "Technoclave 130" from Technorama Company of Fernwald, West Germany and operated at 134° C. at 2 bar for six minutes.
3. An autoclaved tape test specimen is cut to 25.4×127.0 mm.
4. Liner is removed from one side of the test tape specimen and the exposed adhesive strip aligned along and adhered to one of the polyethylene sheets in a strip bordering along the shorter edge. The adhered test tape specimen is rolled twice with a rubber-coated 2 kg roller.
5. The second liner is removed from the test specimen and the adhesive thus exposed is adhered to the second polyethylene sheet in an identical manner, also along the shorter edge. The test sample between the two sheets is rolled twice with the 2 kg roller, completing the adhesive bond to be tested.
6. The two sheets are at this point superimposed. The opposing longer sides are heat sealed to a 4 mm width as described above and trimmed as desired. The two films are heat sealed on opposing sides with the bottom junction adhered together with the test specimen. The top edges of the sheets remain open.

INITIAL ADHESION TO CLOTH

This test can also be described as a 180 degree peel test from linen. An autoclaved sample of linen drape laminate is peeled at an angle of 180 degrees from a cloth-covered substrate. The word initial comes from the fact that the dwell time is short; i.e., the sample is applied and peeled with no long residence time in between. This test simulates a drape to drape bond subjected to peel-type stresses.

A. Preparation of the Substrate

A sample of fluorochemically-treated linen drape material is adhered to a rigid substrate (a stainless steel plate of the sort normally used in the static shear test, in this case) using a section of 3M brand No. 410 Double-coated tape available from Minnesota Mining and Manufacturing Company, St. Paul, Minn. The fabric is tightly adhered to the rigid substrate so that this bond will not fail during the peel test.

B. Preparation of the Sample

Test specimens have liners removed and are applied to the fine weave side of a drape and wrapped with the same material as used in MOISTURE RESISTANCE and autoclaved in the same manner with the same equipment as used in MOISTURE RESISTANCE. Two hours is allowed between the autoclavation and this test.

C. Preparation of the Test Laminate

The sample and the substrate are adhered together.

D. The Test

This test is a modification of Pressure Sensitive Tape Council Test Method PSTC-3, Ninth Edition, Deerfield, Ill., incorporated herein by reference. The modifications are:

1. The steel test panel has been covered with linen drape material to provide a more meaningful substrate for the test. 2. Instead of using a film backing to remove the double-coated tape product from the substrate, a drape material is used to simulate actual use conditions.

The covered plate (substrate) is clamped in one jaw of the tensile tester. End of the sample (autoclaved drape/specimen laminate) is clamped in the other jaw so as to provide a 180 degree peeling action. The jaws of the tensile tester are moved apart in the prescribed manner. The force required to separate the sample from the substrate is recorded. The bond which fails is the one which was formed under PREPARATION OF THE TEST LAMINATE. The test is reported six times for each measurement. Values are recorded in N/2.54 cm or N/inch as called for in Testing Method PSTC-3.

BOND TO CLOTH

This is also a 180 degree peel adhesion test. This time, however, one measures the force required to separate the water-dispersible test specimen from a drape after the two have been autoclaved while adhered together. The autoclave wrapping material and the autoclave conditions are described in MOISTURE RESISTANCE. The test measures the strength of the tape to drape bond which is present in the sterile tape/drape laminate as it comes out of the package in the Operating room. This test is also a modification of Pressure Sensitive Tape Council Test Method PSTC-3.

Exactly as described in Testing Method PSTC-3, (a method especially used for double-coated tapes), a polyester film must be applied to the side opposite to the adhesive bond to be tested in order to help remove the double-coated test specimen from the substrate.

A modification from the prescribed method in Testing Method PSTC-3 is the following: the test substrate in this case is a flexible piece of cloth. In order to provide meaningful results, this substrate must be firmly anchored to a flat inflexible plate. This is accomplished by attaching the side of the drape opposite the adhesive bond to be tested to a steel plate by means of an aggressive auxiliary double-coated tape (3M brand No. 410). Aside from these changes, the bond to cloth test is conducted as in Testing Method PSTC-3.

STATIC SHEAR TEST

Tests of this type are equally well known in the art as the 180 degree peel test. The test method here is a direct derivation of Pressure Sensitive Tape Council Testing Method PSTC-7, incorporated herein by reference. Again the test has been adapted to provide a test substrate which is covered with cloth to simulate actual use conditions.

Preparation of the Substrate

A cloth-covered steel test panel is prepared as described under INITIAL ADHESION test using 3M brand No. 410 double-coated adhesive tape.

Preparation of Sample

The drape/tape laminate is prepared and autoclaved as described under INITIAL ADHESION.

The Test

A shear test is performed is performed using Testing Method PSTC-7 with few modifications. One is the means by which the test bond is formed. Normally the bond is only rolled over twice with the 1 kg roller. In our adapted procedure, the bond is subjected to the pressure of a 1 kg weight for a period of 15 minutes in addition to the normal rolling procedure.

Secondly, the shear test is conducted with a 200 g weight. The automatic timing system used according to Testing Method PSTC-7 records the time when the adhesive bond abruptly fails, simultaneously allowing the weight to fall.

Thirdly, the Testing Method PSTC-7 calls for an adhered area of half by half inch (1.27 cm × 1.27 cm). These tests used an inch by inch (2.54 cm × 2.54 cm) test area.

PROBE TACK TEST AFTER AUTOCLAVATION

Test specimens of the water-dispersible pressure sensitive adhesive tapes prepared according to the procedures described above are placed in an autoclave as in INITIAL ADHESION.

After removal from the autoclave, the samples are placed in a "Polyken Probe Tack Tester" branded inverted probe machine commercially available from Testing Machines Inc. of Mineola, N.Y. The test is conducted according to ASTM D2979-88, which is incorporated by reference.

THUMB TACK TEST

Test specimens of the water-dispersible pressure sensitive adhesive tapes are autoclaved as in MOISTURE RESISTANCE. After removal from the autoclave, the specimens are tested for "thumb tack" by placing an individual's washed and dried thumb on an exposed adhesive surface. The amount of adhesion of the tape to the surface of the thumb is rated using a qualitative assessment of "finger appeal" and assigned a value of 1 through 5 where 1=tack free, 2=poor tack, 3=medium tack, 4=good tack, and 5=excellent tack. On this scale, "Scotch TM " "Magic TM " transparent tape commercially available from Minnesota mining and manufacturing Company has a rating of 5.

WATER DISPERSIBILITY TEST

A 1 m × 1 m linen drape is applied with 1 cm × 10 cm samples of pressure sensitive adhesive tape prepared and autoclaved according to the procedures above. The drape is folded such that the tape is stuck to two sides of the drape. The drape is then folded twice and placed in a Miele washing machine with other test drapes until the washing machine is filled appropriately with garments. Prior to beginning a laundry cycle, each of the filters in the washing machine was checked and cleaned of any residue. The washing machine was set for a cycle of 60 minutes. The laundry cycle include filling of water heated to 80° C. and mixing with a commercially available detergent to create an aqueous alkali solution, followed by agitation in the soapy water, draining, rinsing, and spinning. After laundering, each of the drapes and the filters of the washing machine are examined for any adhesive or fibrous residue.

Preparation of Pressure Sensitive Adhesive

In each example, an acrylate:vinyl carboxylic acid copolymer was prepared, generally as described in U.S. Pat. No. RE 24,906. The monomers to be copolymerized were dissolved in ethylacetate in a one liter bottle. 0.3 weight percent azobisisobutyronitrile (commercially available from DuPont as "Vazo 64") as a polymerization initiator and 0.05 weight percent carbontetrabromide (commercially available from Aldrich or Merck) as a chain transfer agent were added to the liter bottle. A nitrogen purge was introduced for two minutes at a flow rate of 1 liter/min. The solution was held at 55° C. for 24 hours, at which time polymerization was 99% completed. To the solution was then added sufficient methanol and water to produce a solvent system of having a weight ratio 80:15:5, respectively, and to reduce the solids content to about 28-29%.

To the solvent system containing the copolymer solids, were sequentially blended the plasticizer, the tackifier, if any, and the alkali metal hydroxide neutralizing agent(s), if any, in a 4N ethanol and water (60:40 (V/V) EtOH:H$_2$O) solution. The solvent system was agitated with the addition of each item for such mixing times as was necessary to produce a clear, colorless to amber, low viscosity solution.

The resulting pressure sensitive adhesive in the solvent was coated on an area of "Daubert" or "Akrosil" release liner to a thickness of about 100 μm using a standard laboratory knife coater and then dried for ten minutes in a forced air oven at 100° C. The area of adhesive/liner construction was divided. Two areas of the construction were laminated to opposing sides of "Crystex" eight pound basis weight tissue paper, yielding a five layer tape construction of liner, adhesive, tissue paper, adhesive, and liner, sequentially. Each layer of adhesive was about 25 μm thick.

The resultant tape product was then evaluated, using the previously described test procedures.

EXAMPLES 1-30

For convenience, the examples are set forth below in tabular form, all prepared substantially in accordance with the procedure just described, parts and percentages being by weight unless otherwise noted. The effect of varying the types, ratios, and amounts of various components will readily apparent from examining the reported data. The following abbreviations have been employed. TABLE 1 shows the formulations and TABLE 2 shows the performance results. Each result reported in TABLE 2 for each Example is the mean of 6 samples tested.

| | Acrylate Monomer |
|---|---|
| BA | butyl acrylate |
| | Vinyl Carboxylic Acid Monomer |
| AA | acrylic acid |
| | Tackifier |
| AX | colophony acid rosin tackifier, available from Hercules Corporation under the trademark "Foral AX" |
| A 25 | a partially hydrogenated methylstyrene hydrocarbon resin, commercially available from Hercules Corporation under the trademark "Piccolastic A 25" |
| | Plasticizer |
| PE 510 | poly(oxy-1,2-ethandiyl), alpha-(nonylphenyl)-omega-hydroxy-phosphate, available from GAF Corporation under the trademark "Gafac PE 510" |
| LO 529 | poly(oxy-1,2-ethandiyl), alpha-(nonylphenyl)-omega-hydroxy-phosphate sodium, available from GAF Corporation under the trademark "Gafac LO 529" |
| RD 510 | poly(oxy-1,2-ethandiyl), alpha-dodecyl-omega-hydroxy-phosphate, available from GAF Corporation under the trademark "Gafac RD 510" |
| L 62 | colophony polyhydroxy ester rosin tackifier, available from Bergvik under the trademark, "Bevelite L 62" |
| | Neutralizing Agent |
| KOH | |
| NaOH | |
| KOH/NaOH in equimolar amounts | |
| LiOH | |
| LiOH/NaOH in equimolar amounts | |
| | Solvent |
| A | Ethyl Acetate/Methanol/Water in a ratio (V/V) of 80/15/5. |
| B | Ethyl Acetate/Methanol in a ratio (V/V) of 80/20. |

TABLE I

| Example | BA/AA (75/25) Copolymer Parts by Wt | Solvent | Neutralizing Agent | % Copolymer Acid Neutralized | Plasticizer Type | Parts by Wt | Type | Parts by Wt | Tackifier Type | Parts by Wt |
|---|---|---|---|---|---|---|---|---|---|---|
| 1 | 100 | A | NONE | 0 | PE 510 | 89 | — | — | AX | 23 |
| 2 | 100 | A | KOH | 12 | PE 510 | 89 | — | — | AX | 23 |
| 3 | 100 | A | NaOH | 12 | PE 510 | 89 | — | — | AX | 23 |
| 4 | 100 | A | KOH/NaOH | 12 | PE 510 | 89 | — | — | AX | 23 |
| 5 | 100 | A | KOH | 25 | PE 510 | 89 | — | — | AX | 23 |
| 6 | 100 | A | NaOH | 25 | PE 510 | 89 | — | — | AX | 23 |
| 7 | 100 | A | KOH/NaOH | 25 | PE 510 | 89 | — | — | AX | 23 |
| 8 | 100 | A | LiOH | 25 | PE 510 | 89 | — | — | AX | 23 |
| 9 | 100 | A | LiOH/NaOH | 25 | PE 510 | 89 | — | — | AX | 23 |
| 10 | 100 | A | KOH | 50 | PE 510 | 89 | — | — | AX | 23 |
| 11 | 100 | A | NaOH | 50 | PE 510 | 89 | — | — | AX | 23 |
| 12 | 100 | A | KOH/NaOH | 50 | PE 510 | 89 | — | — | AX | 23 |
| 13* | 100 | A | KOH | 100 | PE 510 | 89 | — | — | AX | 23 |
| 14* | 100 | A | NaOH | 100 | PE 510 | 89 | — | — | AX | 23 |
| 15* | 100 | A | KOH/NaOH | 100 | PE 510 | 89 | — | — | AX | 23 |
| 16 | 100 | B | KOH | 25 | PE 510 | 129 | L 62 | 13 | — | — |
| 17 | 100 | B | KOH | 25 | PE 510 | 102 | L 62 | 40 | — | — |
| 18 | 100 | B | KOH | 25 | PE 510 | 93 | L 62 | 29 | — | — |
| 19 | 100 | B | KOH | 25 | PE 510 | 107 | — | — | AX | 11 |
| 20 | 100 | B | KOH | 25 | PE 510 | 136 | — | — | AX | 54 |
| 21 | 100 | B | KOH | 25 | PE 510 | 79 | — | — | AX | 30 |
| 22 | 100 | B | KOH | 25 | PE 510 | 69 | L 62 | 69 | — | — |

TABLE I-continued

| Example | BA/AA (75/25) Copolymer Parts by Wt | Solvent | Neutralizing Agent | % Copolymer Acid Neutralized | Plasticizer Type | Parts by Wt | Type | Parts by Wt | Tackifier Type | Parts by Wt |
|---|---|---|---|---|---|---|---|---|---|---|
| 23 | 100 | B | KOH | 25 | PE 510 | 76 | L 62 | 10 | — | — |
| 24 | 100 | B | KOH | 25 | PE 510 | 76 | L 62 | 36 | — | — |
| 25 | 100 | B | KOH | 25 | PE 510 | 76 | L 62 | 10 | — | — |
| 26 | 100 | B | KOH | 25 | PE 510 | 76 | — | — | A 25 | 10 |
| 27 | 100 | B | KOH | 25 | RD 510 | 76 | L 62 | 10 | — | — |
| 28 | 100 | B | KOH | 25 | LO 529 | 76 | L 62 | 10 | — | — |
| 29 | 100 | B | KOH | 25 | PE 510 | 90 | L 62 | 27 | — | — |
| 30 | 100 | B | KOH | 25 | PE 510 | 90 | L 62 | 27 | — | — |

*Comparative Example

TABLE II

| Example | % Acid Neutralized | Bond to Cloth After Autoclaving (N/2.54 cm) | Initial Adhesion to Cloth After Autoclaving (N/2.54 cm) | Moisture Resistance After Autoclaving (sec./200 ml) | Dispersibility in Soapy Water After Autoclaving | Shear Adhesion to Cloth After Autoclaving (h/200 g) | Polyken Probe Tack Test After Autoclaving (g) | Thumb Tack Test After Autoclaving Scale 1-5 |
|---|---|---|---|---|---|---|---|---|
| 1 | 0 | 16 | 1.0 | 86 | Complete** | 0.3 | — | 5 |
| 2 | 12 | 14.1 | 0.68 | 114 | Complete | 0.5 | 320 | 4 |
| 3 | 12 | 14.3 | 0.85 | 116 | Complete | 0.4 | 300 | 4 |
| 4 | 12 | 10.3 | 0.88 | 136 | Complete | 0.6 | 230 | 4 |
| 5 | 25 | 14.7 | 0.85 | 152 | Complete | 1.6 | 290 | 4 |
| 6 | 25 | 14.2 | 0.84 | 1374 | Complete | 0.7 | 320 | 4 |
| 7 | 25 | 10.9 | 0.90 | 821 | Complete | 0.9 | 240 | 4 |
| 8 | 25 | 12.9 | 0.69 | 60 | Complete | 0.6 | — | 3 |
| 9 | 25 | 12.2 | 0.73 | 68 | Complete | 0.4 | — | 3 |
| 10 | 50 | 8.2 | 0.53 | 143 | Complete | 1.2 | 150 | 3 |
| 11 | 50 | 13.6 | 0.48 | 23 | Complete | 9.8 | 170 | 3 |
| 12 | 50 | 12.7 | 0.53 | 56 | Complete | 3.7 | 100 | 2 |
| 13* | 100 | 14.6 | 0.51 | 29 | Complete | 4.4 | 200 | 2 |
| 14* | 100 | 8.3 | 0.46 | 23 | Complete | 1.1 | 110 | 1 |
| 15* | 100 | 9.9 | 0.31 | 28 | Complete | 0.7 | 120 | 2 |
| 16 | 25 | 13 | 0.4 | 635 | — | 1.2 | — | — |
| 17 | 25 | 13 | 0.6 | 605 | — | 2.3 | — | — |
| 18 | 25 | 11 | 0.4 | 719 | — | 0.7 | — | — |
| 19 | 25 | 11 | 0.9 | 46 | — | — | — | — |
| 20 | 25 | 9 | 0.9 | 1193 | — | — | — | — |
| 21 | 25 | 12 | 1.0 | 750 | — | — | — | — |
| 22 | 25 | 11 | 0.5 | 209 | — | 0.2 | — | — |
| 23 | 25 | 15 | 0.5 | 507 | — | 0.4 | — | — |
| 24 | 25 | 13 | 0.5 | 320 | — | 0.2 | — | — |
| 25 | 25 | 9 | 0.6 | 620 | — | 0.9 | — | — |
| 26 | 25 | 13 | 0.6 | 564 | — | 2.6 | — | — |
| 27 | 25 | 11 | 0.5 | 12*** | — | 1.7 | 270 | — |
| 28 | 25 | 10 | 0.5 | 87 | — | 5.3 | 80 | — |
| 29 | 25 | 8 | 0.8 | 73 | — | 0.8 | — | — |
| 30 | 25 | 9 | 0.8 | 84 | — | 1.1 | — | — |

*Comparative Example
**"Complete" means complete dispersion from cloth without leaving residue on colth or on filters in washing machine.
***Low moisture resistance probably due to loss of adhesion with testing vessel.

Without being limited to the foregoing, the invention is hereby claimed.

What is claimed is:

1. A moisture resistant water-dispersible pressure sensitive adhesive tape capable of retaining pressure sensitive adhesive properties after exposure to autoclavation temperatures, pressures, and humidities comprising:

a hypoallergenic, non-toxic water-dispersible pressure sensitive adhesive coated on at least one surface of a water-dispersible substrate;

the pressure sensitive adhesive being formed from a blend of (a) 100 parts by weight of a copolymer of monomers of (1) about 50–85 weight percent of at least one monomeric acrylic acid ester of nontertiary alkyl alcohol having 2–8 carbon atoms, and (2) about 50–15 weight percent of a vinyl carboxylic acid, (b) about 10 to about 250 parts by weight of a water-dispersible or water-soluble plasticizer comprising a free acid or salt of a complex organic phosphate ester, (c) optionally from about 0 to about 100 parts by weight of an acrylate-compatible tackifier; and (d) sufficient alkali metal hydroxide, if any, to neutralize from 0 to no more than about 38 percent of acid moieties in the copolymer, to cause the adhesive to retain pressure sensitive adhesive properties during exposure to moisture and body fluids yet be dispersible in aqueous alkali solutions.

2. The tape of claim 1, wherein the alkali metal hydroxide is present in an amount which is sufficient to neutralize from about 10 to about 38 percent of acid moieties in the copolymer.

3. The tape of claim 1, wherein the acrylic acid ester comprises butyl acrylate, the vinyl carboxylic acid comprises acrylic acid, and the copolymer has an inherent viscosity of from about 1 to about 2 dl/g for adhering to human skin.

4. The tape of claim 1, wherein the alkali metal hydroxide is present in an amount which is sufficient to neutralize about 25 percent of acid moieties in the copolymer.

5. The tape of claim 4, wherein the pressure sensitive adhesive has a moisture resistance of greater than about 60 seconds during exposure to about 200 ml of water, an initial adhesion to cloth of greater than about 0.6 Newtons/2.54 cm, a bond to cloth of greater than about 1 Newton/2.54 cm, and a static shear adhesion of greater than about 30 minutes during exposure to about 200 g of mass.

6. The tape of claim 2, wherein the alkali metal hydroxide comprises NaOH.

7. The tape of claim 2, wherein the alkali metal hydroxide comprises KOH.

* * * * *